US006852685B1

(12) United States Patent  
Boldogh et al.

(10) Patent No.: US 6,852,685 B1  
(45) Date of Patent: Feb. 8, 2005

(54) USE OF COLOSTRININ, CONSTITUENT PEPTIDES THEREOF, AND ANALOGS THEREOF TO PROMOTE NEURONAL CELL DIFFERENTIATION

(75) Inventors: Istvan Boldogh, Galveston, TX (US); G. John Stanton, Texas City, TX (US); Thomas K. Hughes, Jr., Galveston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 442 days.

(21) Appl. No.: 09/641,802

(22) Filed: Aug. 17, 2000

Related U.S. Application Data

(60) Provisional application No. 60/149,633, filed on Aug. 17, 1999.

(51) Int. Cl.$^7$ ............... A61K 38/00; A61K 38/02; A61K 38/08; A61K 38/18

(52) U.S. Cl. ............... 514/2; 514/12; 514/13; 514/14; 514/15; 514/16; 514/17; 530/300; 530/324; 530/326; 530/327; 530/328; 530/329

(58) Field of Search ............... 514/2, 12, 13, 514/14, 15, 16, 17, 8; 530/300, 324, 326, 327, 328, 329

(56) References Cited

U.S. PATENT DOCUMENTS

| | | | |
|---|---|---|---|
| 4,938,949 A | | 7/1990 | Borch et al. |
| 5,595,887 A | | 1/1997 | Coolidge et al. |
| 6,040,180 A | * | 3/2000 | Johe ............... 435/377 |
| 6,410,058 B2 | | 6/2002 | Gohlke et al. |
| 6,500,798 B1 | | 12/2002 | Stanton et al. |

FOREIGN PATENT DOCUMENTS

| | | | |
|---|---|---|---|
| JP | 06 041191 A | | 2/1994 |
| WO | WO 95/30686 | | 11/1995 |
| WO | WO 98/14473 | * | 4/1998 |
| WO | WO 99/65329 | | 12/1999 |
| WO | WO 00/75173 | | 12/2000 |
| WO | WO 01/11937 | | 2/2001 |
| WO | WO 01/12650 | | 2/2001 |
| WO | WO 01/12651 | | 2/2001 |

OTHER PUBLICATIONS

Rao (1999) "Multipotent and Restricted Precursors in the Central Nervous System." The Anatomical Record (NEW ANAT.) 257: 137–148.*

Schwab, M.E. Repairing the Injured Spinal Cord (2002) Science 295(8): 1029–1031.*

Inglot, A.D., Junsz, M., and Lisowski, J. Colostrinine:a Proline–Rich Polypeptide from Ovine Colostrum Is a Modest Cytokine Inducer in Human Leukocytes (1996) Archivum Immunologiae et Therapiae Experimentalis 44: 215–224.*

Ngo et al. Computational Complexity, Protein Structure Prediction, and the Levinthal Paradox (1994) The Protein Folding Problem and Teriary Structure Prediction (#14), 491–495.*

Wells Addivity of Mutational Effects in Proteins (1990) Biochemistry (29): 37, 8509–8517.*

Kruzel et al. (Dec. 2001) "Towards and Understanding of Biological Role of Colostrinin Peptides." Journal of Molecular Neuroscience 17(3): 379–389.*

Kandel et al. (2002) "Principles of Neural Science." 4th Ed. pp. 67–81, 85–86.*

Bikfalvi et al. (Feb. 1997) "Biological Roles of Fibroblast Growth Factor–2" Endocrine Reviews 18(1): 26–45, especially Section F.*

Popik et al. (Jan. 29, 2001) "Cognitive effects of Colostral–Val nonapeptide in aged rats." Behavioral Brain Research 118(2): 201–208.*

Janusz et al. (1987) mmunoregulatory Properties of Synthetic Peptides, Fragments of a Proline–Rich Polypeptide (PRP) from Ovine Colostrum. Molecular Immnuology 24(10): 1029–1031.*

Inglot, Junsz, and Lisowski Colostrinine:a Proline–Rich Polypeptide from Ovine Colostrum Is a Modest Cytokine Inducer in Human Leukocytes, 1996, Archivum Immunologiae et Therapiae Experimentalis (44) 215–224.*

Elgert, "Immunology: Understanding the Immune System" Text (1996) Wiley–Liss $1^{st}$ Ed. pp. 24–26 and 199–217.*

Altin et al., "Differential Induction of Primary–response (TIS) Genes in PC12 Pheochromocytoma Cells and the Unresponsive Variant PC12nnr5," *Journal of Biological Chemistry*, Mar. 25, 1991; 266(9): 5401–5406.

Anneren et al., "GTK, a Src–related Tyrosine Kinase, Induces Nerve Growth Factor–independent Neurite Outgrowth in PC 12 Cells through Activation of the Rap1 Pathway," *Journal of Biological Chemistry*, Sep. 15, 2000;275(37): 29153–29161.

Bagchi et al., "Comparative in vitro and in vivo protein kinase C activation by selected pesticides and transition metal salts," *Toxicology Letters*, 1997;91: 31–37.

Chen et al., "Lithium Increase Tyrosine Hydroxylase Levels both In Vivo and In Vitro," *Journal of Neurochemistry*, 1998;70(4): 1768–1771.

Cui et al., "Effect of Nucleoside Analogs on Neurite Regeneration and Mitochondrial DNA Synthesis in PC–12 Cells," *Journal of Pharmacology and Experimental Therapeutics*, 1997;280(3): 1228–1234.

Dagø et al., "NS 1231, a novel compound with neurotrophic–like effects in vitro and in vivo," *Journal of Neurochemistry*, 2002;81: 17–24.

(List continued on next page.)

*Primary Examiner*—Brenda Brumback  
*Assistant Examiner*—Christopher James Nichols  
(74) *Attorney, Agent, or Firm*—Mueting, Raasch & Gebhardt, P.A.

(57) ABSTRACT

The present invention discloses a use of colostrinin, a constituent peptide thereof, and/or an analog thereof as a neural cell regulator in animals including humans.

24 Claims, 1 Drawing Sheet

OTHER PUBLICATIONS

DeJongh et al., "Estimation of Systemic Toxicity of Acrylamide by Integration of in vitro Toxicity Data with Kinetic Simulations," *Toxicology and Applied Pharmacology,* 1999;158: 261–268.

Doye et al., "Phosphorylation of Stathmin and Other Proteins Related to Nerve Growth Factor–induced Regulation of PC12 Cells," *Journal of Biological Chemistry,* Jul. 15, 1990;265(20): 11650–11655.

Feng et al., "NF–κB/Rel Proteins are Required for Neuronal Differentiation of SH–SY5Y Neuroblastoma Cells," *Journal of Biological Chemistry,* Oct. 22, 1999;274(43): 30341–30344.

Kim et al., "Insulin–like Growth Factor–I–mediated Neurite Outgrowth in Vitro Requires Mitogen–activated Protein Kinase Activation," *Journal of Biological Chemistry,* Aug. 22, 1997;272(34): 21268–21273.

Kim et al., "Differential Regulation of Insulin Receptor Substrate–2 and Mitogen–Activated Protein Kinase Tyrosine Phosphorylation by Phosphatidylinositol 3–Kinase Inhibitors in SH–SY5Y Human Neuroblastoma Cells," *Endocrinology,* 1998;139(12): 4881–4889.

Lachyankar et al., "A Role for Nuclear PTEN in Neuronal Differentiation," *Journal of Neuroscience,* Feb. 15, 2000;20(4): 1404–1413.

Noble et al., "Overexpression of Dynamin is Induced by Chronic Stimulation of μ– but Not δ–Opioid Receptors: Relationships with μ–Related Morphine Dependence," *Molecular Pharmacology,* 2000;58: 159–166.

Ponthan et al., "The Synthetic Retinoid RO 13–6307 induces Neuroblastoma Differentiation in vitro and inhibits Neuroblastoma Tumour growth in vivo," *Int. J. Cancer,* 2003;104: 418–424.

Puglianiello et al., "IGF–I stimulates chemotasix of human neuroblasts. Involvement of type 1 IGF receptor, IGF binding proteins, phosphatidylinositol–3 kinase pathway and plasmin system," *Journal of Endocrinology,* 2000;165: 123–131.

Xiang–Ming et al., "Gating kinetics of potassium channel and effects of nerve growth factors in PC12 cells analyzed with fractal model," *Acta Pharmacol Sin,* Feb. 2001;22(2): 103–110.

Zhen et al., "Lithium regulates protein tyrosine phosphatase activity in vitro and in vivo," *Psychopharmacology,* 2002;162: 379–384.

Cosgaya et al., "Neuronal differentiation of PC12 cells induced by engrailed homeodomain is DNA–binding specific and independent of MAP kinases," *Journal of Cell Science* 1998; 111: 2377–2384.

Elgert, "Immunology: Understanding the Immune System," Text (1996) Wiley–Liss 1st Ed. pp. 24–26 and 199–217.

Kimball, John W., "White Blood Cells (leukocytes)," *Kimball's Biology Papers* [online]. [retrieved on Dec. 2, 2000]. 2 pgs.

Leszek et al., "Colostrinin® proline–rich polypeptide compley from ovine colostrum– a long–term study of its efficacy in Alzheimer's disease," *Med Sci Monit.,* 2002;8(10): 193–196.

Vaudry et al., "Signaling Pathways for PC12 Cell Differentiation: Making the Right Connections," *Science* May 31, 2002;296: 1648–1649.

Babbit, ed., *The Vanderbilt Rubber Handbook,* R.T. Vanderbilt Company, Inc., Norwalk, CT, pp. 344–397 (1978).

Bespalov et al., "Fabs specific for 8–oxoguanine: control of DNA binding," *J Mol Biol.* Nov. 12, 1999; 293(5):1085–95.

Blach–Olszewska et al., "Stimulatory effect of ovine colostrinine (a proline–rich polypeptide) on interferons and tumor necrosis factor production by murine resident peritoneal cells," *Arch Immunol Ther Exp* (Warsz), 1997;45(1):43–7.

Buescher et al., "Colostral antioxidants: separation and characterization of two activities in human colostrum," *J Pediatr Gastroenterol Nutrl.* Jan. 1992; 14(1):47–56.

Calingasan et al., "Protein–bound acrolein: a novel marker of oxidative stress in Alzheimer's disease," *J Neurochem.* Feb. 1999;72(2):751–6.

Chao "Growth factor signaling: where is the specificity?" *Cell.* Mar. 20, 1992;68(6):995–7.

Esterbauer et al., "Chemistry and biochemistry of 4–hydroxynonenal, malonaldehyde and related aldehydes," *Free Radic Biol Med. 1991;* 11(1):81–128.

Fields et al., *Synthetic Peptides: A User's Guide,* W.M. Freeman & Company, New York, NY, pp. 77–183 (1992).

Fillmore et al., "Differentiation of PC12 cells with nerve growth factor is associated with induction of transin synthesis and release," *J Neurosci Res.* Apr. 1992;31(4):662–9.

Gabbita et al., "Increased nuclear DNA oxidation in the brain in Alzheimer's disease," *J Neurochem.* Nov. 1998;71(5):2034–40.

Gabbita et al., "Decrease in peptide methionine sulfoxide reductase in Alzheimer's disease brain," *J. Neurochem.* Oct. 1999;73(4):1660–6.

Good et al., "Evidence of neuronal oxidative damage in Alzheimer's disease," *Am J Pathol.* Jul. 1996;149(1):21–8.

Gratama et al., "Flow cytometric quantitation of immunofluorescence intensity: problems and perspectives. European Working Group on Clinical Cell Analysis," *Cytometry.* Oct. 1, 1998;33(2):166–78.

Grunwald et al., "In situ analysis of chromatin proteins during development and cell differentiation using flow cytometry," *Methods Mol Biol.* 1999; 119:443–54.

Hensley et al., "Brain regional correspondence between Alzheimer's disease histopathology and biomarkers of protein oxidation," *J Neurochem.* Nov. 1995; 65(5):2146–56.

Hughes et al., "Modulation of immune responses by anabolic androgenic steroids," *Int J Immunopharmacol.* Nov. 1995;17(11):857–63.

Inglot et al., "Colostrinine: a proline–rich polypeptide from ovine colostrum is a modest cytokine inducer in human leukocytes," *Arch Immunol Ther Exp* (Warsz). 1996;44(4):215–24.

Inglot et al., "Colostrinin for treatment of Alzheimer's disease," *European Cytokine Network.* Sep. 1996;7(3):458 (abstract 51).

Inglot et al., "Tumor–associated antigens are cytokine inducers and hyporeactivity factors to the immune system," *Biotherapy,* 1998;11(1):27–37.

Janusz et al., "Isolation and characterization of a proline–rich polypeptide from ovine colostrum," *FEBS Lett.* Dec. 15, 1974;49(2):276–9.

Janusz, et al., "Chemical and physical characterization of a proline–rich polypeptide from sheep colostrum," *Biochem J.* Oct. 1, 1981; 199(1):9–15.

Janusz et al., "Proline–rich polypeptide (PRP)—an immunomodulatory peptide from ovine colostrum," *Arch Immunol Ther Exp* (Warsz). 1993;41(5–6):275–9.

Kim et al., "Simultaneous differentiation and quantitation of erythroblasts and white blood cells on a high throughput clinical haematology analyser," *Clin Lab Haematol.* Feb. 1998; 20(1):21–9.

Kooy et al., "Oxidation of 2',7'–dichlorofluorescin by peroxynitrite," *Free Radic Res.* Sep. 1997;27(3):245–54.

LeBel et al., "Evaluation of the probe 2',7'–dichlorofluorescin as an indicator of reactive oxygen species formation and oxidative stress," *Chem Res Toxicol.* Mar.–Apr. 1992;5(2):227–31.

Leszek et al., "Colostrinin: a proline–rich polypeptide (PRP) complex isolated from ovine colostrum for treatment of Alzheimer's disease. A double–blind, placebo–controlled study," *Arch Immunol Ther Exp (Warsz).* 1999;47(6):377–85.

Levi et al., "The mode of action of nerve growth factor in PC12 cells," *Mol Neurobiol.* 1998 Fall;2(3):201–26.

Lovell et al., "Elevated thiobarbituric acid–reactive substances and antioxidant enzyme activity in the brain in Alzheimer's disease," *Neurology.* Aug. 1995; 45(8):1594–601.

Lovell et al., "Elevated 4–hydroxynonenal in ventricular fluid in Alzheimer's disease," *Neurobiol Aging.* Sep.–Oct. 1997;18(5):457–61.

Lovell et al., "Decreased glutathione transferase activity in brain and ventricular fluid in Alzheimer's disease," *Neurology.* Dec. 1998;51(6):1562–6.

Lovell et al., "Increased DNA oxidation and decreased levels of repair products in Alzheimer's disease ventricular CSF," *J. Neurochem.* Feb. 1999;72(2):771–6.

Lovell et al., "Decreased base excision repair and increased helicase activity in Alzheimer's disease brain," *Brain Res.* Feb. 7, 2000;855(1):116–23.

Markesberry, "Oxidative stress hypothesis in Alzheimer's disease," *Free Radic Biol Med.* 1997;23(1):134–47.

Markesbery et al., "Four–hydroxynonenal, a product of lipid peroxidation, is increased in the brain in Alzheimer's disease," *Neurobiol Aging.* Jan.–Feb. 1998;19(1):33–6.

Markesbery et al. "Oxidative alterations in Alzheimer's disease," *Brain Pathol.* Jan. 1999;9(1):133–46.

Marshall et al., "Specificity of receptor tyrosine kinase signaling: transient versus sustained extracellular signal-regulated kinase activation," *Cell.* Jan. 27, 1995;80(2):179–85.

McHeyzer–Williams et al., "Enumeration and characterization of memory cells in the TH compartment," *Immunol Rev.* Apr. 1996;150:5–21.

Mecocci et al., "Oxidative damage to mitochondrial DNA is increased in Alzheimer's disease," *Ann Neurol.* Nov. 1994;36(5):747–51.

Mishell et al., *Selected Methosd in Cellular Immunology,* W.H. Freeman, San Francisco, CA; title page and table of contents only, 9 pages (1980).

Montine et al., "Cerebrospinal fluid F2–isoprostane levels are increased in Alzheimer's disease," *Ann Neurol.* Sep. 1998; 44(3):410–3.

Ostrea et al., "Influence of breast–feeding on the restoration of the low serum concentration of vitamin E and beta–carotene in the newborn infant," *Am J Obstet Gynecol.* May 1986;154(5):1014–7.

Peunova et al., "Nitric oxide triggers a switch to growth arrest during differentiation of neuronal cells," *Nature.* May 4, 1995;375(6526):68–73.

Piasecki et al., "Coincidence between spontaneous release of interferon and tumor necrosis factor by colostral leukocytes and the production of a colostrinine by human mammary gland after normal delivery," *Arch Immunol Ther Exp (Warsz).* 1997;45(1):109–17.

Popik et al., "Colostrinin, a polypeptide isolated from early milk, facilitates learning and memory in rats," *Pharmacol Biochem Behav.* Sep. 1999;64(1):183–9.

Prasad et al., "Regional membrane phospholipid alterations in Alzheimer's disease," *Neurochem Res.* Jan. 1998;23(1):81–8.

Roberts II et al., "Formation of isoprostane–like compounds (neuroprostanes) in vivo from docosahexaenoic acid," *J Biol Chem.* May 29, 1998;273(22):13605–12.

Rothe et al., "Flow cytometric analysis of respiratory burst activity in phagocytes with hydroethidine and 2',7'–dichlorofluorescin," *J Leukoc Biol.* May 1990;47(5):440–8.

Royall et al., "Evaluation of 2',7'–dichlorofluorescin and dihydrorhodamine 123 as fluorescent probes for intracellular H2O2 in cultured endothelial cells," *Arch Biochem Biophys.* May 1993;302(2):348–55.

Subbarao et al., "Autopsy samples of Alzheimer's cortex show increased peroxidation in vitro," *J Neurochem.* Jul. 1990; 55(1):342–5.

Shacter et al., "Differential susceptibility of plasma proteins to oxidative modification: examination by western blot immunoassay," *Free Radic Biol Med.* Nov. 1994;17(5):429–37.

Singh et al., "Dietary intake, plasma levels of antioxidant vitamins, and oxidative stress in relation to coronary artery disease in elderly subjects," *Am J Cardiol.* Dec. 15, 1995;76(17):1233–8.

Smith et al., "Advanced Maillard reaction end products are associated with Alzheimer disease pathology," *Proc Natl Acad Sci U S A.* Jun. 7, 1994; 91(12):5710–4.

Smith et al., "Oxidative damage in Alzheimer's," *Nature.* Jul. 11, 1996; 382(6587):120–1.

Smith et al., "Excess brain protein oxidation and enzyme dysfunction in normal aging and in Alzheimer disease," *Proc Natl Acad Sci U S A.* Dec. 1, 1991; 88(23):10540–3.

Svennerholm et al., Membrane lipids, selectively diminished in Alzheimer brains, suggest synapse loss as a primary event in early–onset form (type I) and demyelination in late–onset form (type II), *J Neurochem.* Mar. 1994; 62(3):1039–47.

Takahashi et al., "Spontaneous transformation and immortalization of human endothelial cells," *In Vitro Cell Dev Biol.* Mar. 1990;26(3 Pt 1):265–74.

Tsuchiya et al., "In vivo visualization of oxygen radical–dependent photoemission," *Methods Enzymol (Oxygen Radicals in Biological Systems).* 1994;233C:128–40.

Villas et al., "Flow cytometry: an overview" *Cell Vis.* Jan.–Feb. 1998;5(1):56–61.

Yan et al., "Glycated tau protein in Alzheimer disease: a mechanism for induction of oxidant stress," *Proc Natl Acad Sci U S A.* Aug. 2, 1994;91(16):7787–91.

Zimecki et al., "Effect of a proline–rich polypeptide (PRP) on the development of hemolytic anemia and survival of New Zealand black (NZB) mice," *Arch Immunol Ther Exp (Warsz).* 1991;39(5–6):461–7.

* cited by examiner

Effect of NGF and Constituent Peptides of Colostrinin on Morphology of PC12 Cells A: Control
B: NGF (100 ng/ml)
C: SEQ ID NO:1 (1 micro g/ml)
D: SEQ ID NO:2 (1 micro g/ml)
D1: SEQ ID NO:2 (0.1 micro g/ml)

USE OF COLOSTRININ, CONSTITUENT PEPTIDES THEREOF, AND ANALOGS THEREOF TO PROMOTE NEURONAL CELL DIFFERENTIATION

CROSS-REFERENCE TO RELATED APPLICATIONS

The present application claims priority from U.S. patent application Ser. No. 60/149,633, filed on Aug. 17, 1999, which is incorporated herein by reference.

BACKGROUND OF THE INVENTION

Colostrum is a component of the milk of mammals during the first few days after birth. Colostrum is a thick yellowish fluid and is the first lacteal secretion post parturition and contains a high concentration of immunogloblins (IgG, IgM, and IgA) and a variety of non-specific proteins. Colostrum also contains various cells such as granular and stromal cells, neutrophils, monocyte/macrophages, and lymphocytes. Colostrum also includes growth factors, hormones, and cytokines. Unlike mature breast milk, colostrum contains low sugar, low iron, but is rich is lipids, proteins, mineral salts, vitamins, and immunoglobins.

Colostrum also includes or contains a proline-rich polypeptide aggregate or complex, which is referred to as colostrinin. One peptide fragment of colostrinin is Val-Glu-Ser-Tyr-Val-Pro-Leu-Phe-Pro (SEQ ID NO:31), which is disclosed in International Publication No. WO-A-98/14473. Colostrinin and this fragment have been identified as useful in the treatment of disorders of the central nervous system, neurological disorders, mental disorders, dementia, neurodegenerative diseases, Alzheimer's disease, motor neurone disease, psychosis, neurosis, chronic disorders of the immune system, diseases with a bacterial and viral aetiology, and acquired immunological deficiencies as set forth in International Publication No. WO-A-98/14473.

Although certain uses for colostrinin have been identified, it would represent an advancement in the art to discover and disclose other uses for colostrinin, or a component thereof, that are not readily ascertainable from the information currently known about colostrinin or its constituents.

SUMMARY OF THE INVENTION

The present invention relates to the use of colostrinin, at least one constituent (i.e., component) peptide thereof, at least one active analog thereof (e.g., peptide having an N-terminal sequence equivalent to an N-terminal sequence of at least one of the colostrinin constituent peptides), and combinations thereof, as promoters of neural cell differentiation. These agents can be used in vitro or in vivo, including internal use in patients, particularly animals (including mammals such as humans).

In one embodiment, the present invention provides a method for promoting cell differentiation. The method includes contacting cells (preferably, pluripotent cells) with a neural cell regulator selected from the group of colostrinin, a constituent peptide thereof, an analog thereof, and combinations thereof, under conditions effective to change the cells in morphology to form neural cells (i.e., nerve-like cells). The cells can be present in a cell culture, an organ, a tissue, or an organism. Preferably, the cells are mammalian cells, and more preferably, human cells. The neural cell regulator is preferably a constituent peptide of colostrinin, such as those described herein (SEQ ID NOs:1–34).

The present invention also provides a method for promoting neural cell differentiation in a patient (preferably, a human). The method includes administering to the patient a neural cell regulator selected from the group of colostrinin, a constituent peptide thereof, an analog thereof, and combinations thereof, under conditions effective to promote differentiation (i.e., a change in morphology) of cells to form neural cells (i.e., nerve-like cells).

The present invention further provides a method for treating damaged (which typically possess less than complete function and may be completely nonfunctional) neural cells. The method includes contacting damaged neural cells with a neural cell regulator selected from the group of colostrinin, a constituent peptide thereof, an analog thereof, and combinations thereof, under conditions effective to convert the damaged neural cells to functional neural cells. This method can occur in vitro or in vivo. An in vivo method for treating damaged (e.g., nonfunctional) neural cells in a patient includes administering to the patient a neural cell regulator selected from the group of colostrinin, a constituent peptide thereof, an analog thereof, and combinations thereof, under conditions effective to convert damaged neural cells to functional neural cells.

In other embodiments, the invention provides the use of a neural cell regulator in the manufacture of a medicament for use in the methods described herein.

As used herein, "neural" and "nerve-like" are used interchangeably. Such cells have morphologies resembling nerve cells. For example, a central body with neurite outgrowth. As used herein, nonfunctional neural cells are those that do not trasmit information by, e.g., acetylcholine, but morphologically resemble nerve cells, and functional neural cells are those that do trasmit information using mediators such as acetylcholine and morphologically resemble nerve cells.

As used herein, "a" or "an" means one or more, such that combinations of active agents (i.e., active immunological regulators or blood cell differentiation promoters), for example, can be used in the compositions and methods of the invention. Thus, a composition that includes "a" polypeptide refers to a composition that includes one or more polypeptides.

"Amino acid" is used herein to refer to a chemical compound with the general formula: $NH_2$—CRH—COOH, where R, the side chain, is H or an organic group. Where R is organic, R can vary and is either polar or nonpolar (i.e., hydrophobic). The amino acids of this invention can be naturally occurring or synthetic (often referred to as nonproteinogenic). As used herein, an organic group is a hydrocarbon group that is classified as an aliphatic group, a cyclic group or combination of aliphatic and cyclic groups. The term "aliphatic group" means a saturated or unsaturated linear or branched hydrocarbon group. This term is used to encompass allyl, alkenyl, and alkynyl groups, for example. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" refers to mono- or polycyclic aromatic hydrocarbon groups. As used herein, an organic group can be substituted or unsubstituted.

The terms "polypeptide" and "peptide" are used interchangeably herein to refer to a polymer of amino acids. These terms do not connote a specific length of a polymer of amino acids. Thus, for example, the terms oligopeptide, protein, and enzyme are included within the definition of polypeptide or peptide, whether produced using recombinant techniques, chemical or enzymatic synthesis, or naturally occurring. This term also includes polypeptides that have been modified or derivatized, such as by glycosylation, acetylation, phosphorylation, and the like.

The following abbreviations are used throughout the application:

| | |
|---|---|
| A = Ala = Alanine | T = Thr = Threonine |
| V = Val = Valine | C = Cys = Cysteine |
| L = Leu = Leucine | Y = Tyr = Tyrosine |
| I = Ile = Isoleucine | N = Asn = Asparagine |
| P = Pro = Proline | Q = Gln = Glutamine |
| F = Phe = Phenylalanine | D = Asp = Aspartic Acid |
| W = Trp = Tryptophan | E = Glu = Glutamic Acid |
| M = Met = Methionine | K = Lys = Lysine |
| G = Gly = Glycine | R = Arg = Arginine |
| S = Ser = Serine | H = His = Histidine |

DETAILED DESCRIPTION OF PREFERRED EMBODIMENTS

Figure 1:
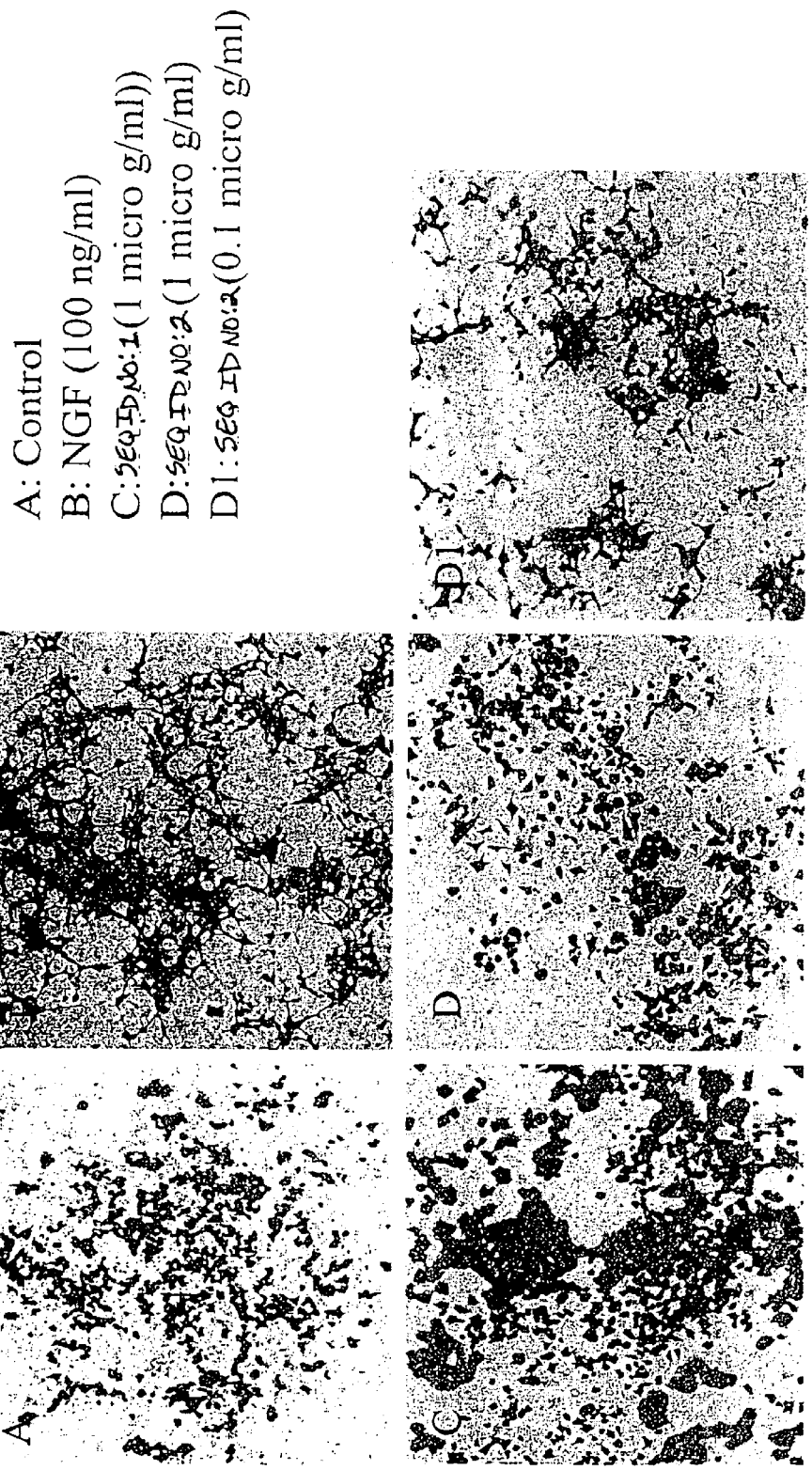
FIG. 1. Effect of NGF and constituent peptides of colostrinin on morphology of PC12 cells. $3 \times 10^4$ cells per well were seeded in 24× well plates and 24 hours (h) later cells were treated with NGF or colostrinin, colostrinin, or its constituent peptides, as described in the Examples Section. Six days after treatment, cells were fixed in formaldehyde and stained to visualize morphological changes of cells. Mock-treated cells (A), NGF-treated cells (13). Lower panel demonstrate typical morphological changes of PC12 cells after exposure to SEQ ID NO:1 (C) or SEQ ID NO:2 (D, D1).
Figure 1:
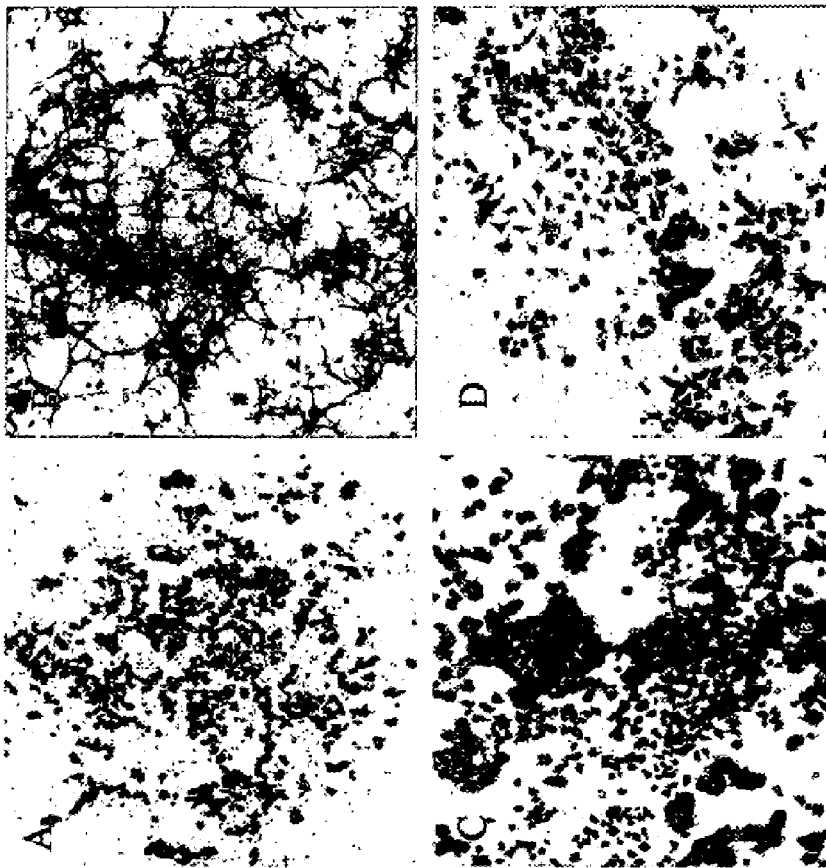

The inventors have found that colostrinin, at least one constituent peptide thereof, and/or at least one active analog thereof (e.g., a peptide having an N-terminal sequence equivalent to an N-terminal sequence of at least one of the colostrinin constituent peptides) can be used as neural cell regulators. Such regulators promote the differentiation of cells (e.g., pluripotent cells) such that there is a change in morphology to form neural cells (which can be present in tissues and organs such as brain or ganglion). This can occur in vitro or in vivo, including internally in animals (including mammals such as humans). These regulators can also convert damaged (e.g., nonfunctional) neural cells to functional neural cells.

Such neural cell regulators are referred to herein as "active agents." Significantly, such agents can be administered alone or in various combinations to a patient (e.g., animals including humans) as a medication or dietary (e.g., nutrient) supplement in a dose sufficient to cause nerve cell increase throughout the patient's body, in a specific tissue site, or in a collection of tissues (organs).

The differentiation process of cells in the nervous system is regulated by the action of differentiation and growth factors including NGF. For example, NGF binding to its receptor tyrosine kinase, TrkA, initiates various molecular interactions including tyrosine phosphorylation of proteins and the action of the Ras/Raf/MEK/MAPK pathway (Chao, Cell, 68, 995–997 (1992); and Marshall et al., Cell, 80, 179–185 (1995)). NGF induces the production of reactive nitric oxide (NO), and NO is required for NGF-induced cytostasis and differentiation (Peunova et al., Nature. 375, 68–73 (1995)), suggesting that free radical molecules may exert a regulatory role in certain types of cellular differentiation.

It is important to promote nerve cell differentiation (i.e., promote differentiation of cells to form neural cells) and/or conversion of damaged nerve cells where there has been significant damage to nerve cells that can occur in a wide variety of situations. The active agents described herein can be used individually, in various combinations, or combined with other previously known or newly invented pharmacological agents. The promotion of nerve cell differentiation responses can be taken advantage of, for example, in cell, tissue, or organ regeneration, repair, and replacement.

In preferred embodiments, the present invention provides methods for promoting neural cell differentiation (i.e., differentiation of cells to form neural cells) and converting nonfunctional neural cells to functional neural cells. Whether it be in vivo or in vitro, these methods involve monitoring the level of increase in functional nerve cells and/or changes in the morphology of cells formed using phenotypic markers as disclosed by Fillmore et al., J. Neurosci. Res., 31, 662–669 (1992) and Levi et al., Mol. Neurobiol., 2, 201–226 (1988). Specific in vitro methods are described in the Examples Section.

Colostrinin is composed of peptides, the aggregate of which has a molecular weight range between about 5.8 to about 26 kiloDaltons (kDa) determined by polyacrylamide gel electrophoresis. It has a greater concentration of proline than any other amino acid. Ovine colostrinin has been found to have a molecular weight of about 18 kDa and includes three non-covalently linked subunits having a molecular weight of about 6 kDa and has about 22 wt-% proline. Ovine colostrum has also been shown to contain the following number of residues per subunit: lysine-2; histidine-1; arginine-0; aspartic acid-2; threonine-4; serine-3; glutamic acid-6; proline-11; glycine-2; alanine-0; valine-5; methionine-2; isoleucine-2; leucine-6; tyrosine-1; phenylalanine-3; and cysteine-0.

Colostrinin has been found to include a number of peptides ranging from 3 amino acids to 22 amino acids or more. These can be obtained by various known techniques, including isolation and purification involving eletrophoresis and synthetic techniques. The specific method of obtaining colostrinin and SEQ ID NO:31 is described in International Publication No. WO-A-98/14473. Using HPLC and Edelman Degradation, over 30 constituent peptides of colostrinin have been identified, which can be classified into several groups: (A) those of unknown precursor; (B) those having a β-casein homologue precursor; (C) those having a β-casein precursor; and (D) those having an annexin precursor. These peptides are described in International Patent Publication No. WO 00/75173, filed Jun. 2, 2000, claiming priority to Jun. 2, 1999, and can be synthesized according to the general method described in the Examples Section. These peptides (i.e., constituent peptides of colostrinin), which can be derived from colostrinin or chemically synthesized, include: MQPPPLP (SEQ ID NO:1); LQTPQPLLQVMMEPQGC (SEQ ID NO:2); DQPPDVEKPDLQPFQVQS (SEQ ID NO:3); LFFFLPVVNVLP (SEQ ID NO:4); DLEMPV-LPVEPFPFV (SEQ ID NO:5); MPQNFYKLPQM (SEQ ID NO:6); VLMKFPPPPQETVT (SEQ ID NO:7); LKPFP-KLKVEVFPFP (SEQ ID NO:8); VVMEV (SEQ ID NO:9); SEQP (SEQ ID NO:10); DKE (SEQ ID NO:11); FPPPK (SEQ ID NO:12); DSQPPV (SEQ ID NO:13); DPPPPQS (SEQ ID NO:14); SEEMP (SEQ ID NO:15); KYKLQPE (SEQ ID NO:16); VLPPNVG (SEQ ID NO:17); VYPFTG-PIPN (SEQ ID NO:18); SLPQNILPL (SEQ ID NO:19); TQTPVVVPPF (SEQ ID NO:20); LQPEIMGVPKVKET-MVPK (SEQ ID NO:21); YKEMPFPKYPVEPFTESQ (SEQ ID NO:22); SLTLTDVEKLHLPLPLVQ (SEQ DD NO:23); SWMHQPP (SEQ ID NO:24); QPLPPTVMFP (SEQ ID NO:25); PQSVLS (SEQ ID NO:26); LSQPKV-LPVPQKAVPQRDMPIQ (SEQ ID NO:27); AFLLYQE (SEQ ID NO:28); RGPFPILV (SEQ ID NO:29); ATFN-RYQDDHGEEILKSL (SEQ ID NO:30); VESYVPLFP (SEQ ID NO:31); FLLYQEPVLGPVR (SEQ ID NO:32); LNF (SEQ ID NO:33); and MHQPPQPLPPTVMFP (SEQ ID NO:34). These can be classified as follows: (A) those of unknown precursor include SEQ ID NOs:2, 6, 7, 8, 10, 11, 14, and 33; (B) those having a β-casein homologue precursor include SEQ ID NOs:1, 3, 4, 5, 9, 12, 13, 15, 16, 17, and 31; (C) those having β-casein precursor include SEQ ID NOs:18 (casein amino acids 74–83), 19 (casein amino acids 84–92), 20 (casein amino acids 93–102), 21 (casein amino acids 103–120), 22 (casein amino acids 121–138), 23 (casein amino acids 139–156), 24 (casein amino acids 157–163), 25 (casein amino acids 164–173), 26 (casein amino acids 174–179), 27 (casein amino acids 180–201), 28 (casein amino acids 202–208), 29 (casein amino acids 214–222), 32 (casein amino acids 203–214), and 34 (casein amino acids 159–173); and (D) those having an annexin precursor include SEQ ID NO:30 (annexin amino acids 203–220).

A preferred group of such peptides includes: MQPPPLP (SEQ ID NO:1); LQTPQPLLQVMMEPQGD (SEQ ID NO:2); DQPPDVEKPDLQPFQVQS (SEQ ID NO:3); LFF-FLPVVNVLP (SEQ ID NO:4); DLEMPVLPVEPFPFV (SEQ ID NO:5); MPQNFYKLPQM (SEQ ID NO:6); VLEMKFPPPPQETVT (SEQ ID NO:7); LKPFP-KLKVEVFPFP (SEQ ID NO:8); and combinations thereof.

The polypeptides of SEQ ID NOs:1–34 can be in their free acid form or they can be amidated at the C-terminal carboxylate group. The present invention also includes analogs of the polypeptides of SEQ ID NOs:1–34, which includes polypeptides having structural similarity with SEQ ID NOs:1–34. These peptides can also form a part of a larger peptide. An "analog" of a polypeptide includes at least a portion of the polypeptide, wherein the portion contains deletions or additions of one or more contiguous or non-contiguous amino acids, or containing one or more amino acid substitutions. An "analog" can thus include additional amino acids at one or both of the termini of the polypeptides listed above. Substitutes for an amino acid in the polypeptides of the invention are preferably conservative substitutions, which are selected from other members of the class to which the amino acid belongs. For example, it is well-known in the art of protein biochemistry that an amino acid belonging to a grouping of amino acids having a particular size or characteristic (such as charge, hydrophobicity, and hydrophilicity) can generally be substituted for another amino acid without substantially altering the structure of a polypeptide.

For the purposes of this invention, conservative amino acid substitutions are defined to result from exchange of amino acids residues from within one of the following classes of residues: Class I: Ala, Gly, Ser, Thr, and Pro (representing small aliphatic side chains and hydroxyl group side chains); Class II: Cys, Ser, Thr and Tyr (representing side chains including an —OH or —SH group); Class III: Glu, Asp, Asn and Gln (carboxyl group containing side chains): Class IV: His, Arg and Lys (representing basic side chains); Class V: Ile, Val, Leu, Phe and Met (representing hydrophobic side chains); and Class VI: Phe, Trp, Tyr and His (representing aromatic side chains). The classes also include related amino acids such as 3Hyp and 4Hyp in Class I; homocysteine in Class II; 2-aminoadipic acid, 2-aminopimelic acid, γ-carboxyglutamic acid, β-carboxyaspartic acid, and the corresponding amino acid amides in Class III; ornithine, homoarginine, N-methyl lysine, dimethyl lysine, trimethyl lysine, 2,3-diaminopropionic acid, 2,4-diaminobutyric acid, homoarginine, sarcosine and hydroxylysine in Class IV; substituted phenylalanines, norleucine, norvaline, 2-aminooctanoic acid, 2-aminoheptanoic acid, statine and β-valine in Class V; and naphthylalanines, substituted phenylalanines, tetrahydroisoquinoline-3-carboxylic acid, and halogenated tyrosines in Class VI.

Preferably, the active analogs of colostrinin and its constituent peptides include polypeptides having a relatively large number of proline residues. Because proline is not a common amino acid, a "large number" preferably means that a polypeptide includes at least about 15% proline (by number), and more preferably at least about 20% proline (by number). Most preferably, active analogs include more proline residues than any other amino acid.

As stated above, active analogs of colostrinin and its constituent peptides include polypeptides having structural similarity. Structural similarity is generally determined by aligning the residues of the two amino acid sequences to optimize the number of identical amino acids along the lengths of their sequences; gaps in either or both sequences are permitted in making the alignment in order to optimize the number of identical amino acids, although the amino acids in each sequence must nonetheless remain in their proper order. Preferably, two amino acid sequences are compared using the Blastp program, version 2.0.9, of the BLAST 2 search algorithm, available on the worldwide web at ncbi.nlm.nih.gov/gorf/b12.html. Preferably, the default values for all BLAST 2 search parameters are used, including matrix=BLOSUM62; open gap penalty=11, extension gap penalty=1, gap x_dropoff=50, expect=10, wordsize=3, and filter on. In the comparison of two amino acid sequences using the BLAST search algorithm, structural similarity is referred to as "identity." Preferably, an active analog of colostrinin or its constituent peptides has a structural similarity to colostrinin or one or more of its constituent peptides (preferably, one of SEQ ID NOs:1–34) of at least about 70% identity, more preferably, at least about 80% identity, and most preferably, at least about 90% identity.

Colostrinin or any combination of its peptide components or active analogs thereof can be derived (preferably, isolated and purified) naturally such as by extraction from colostrum or can be synthetically constructed using known peptide polymerization techniques. For example, the peptides of the invention may be synthesized by the solid phase method using standard methods based on either t-butyloxycarbonyl (BOC) or 9-fluorenylmethoxy-carbonyl (FMOC) protecting groups. This methodology is described by G. B. Fields et al. in *Synthetic Peptides: A User's Guide*, W. M. Freeman & Company, New York, N.Y., pp. 77–183 (1992). Moreover, gene sequence encoding the colostrinin peptides or analogs thereof can be constructed by known techniques such as expression vectors or plasmids and transfected into suitable microorganisms that will express the DNA sequences thus preparing the peptide for later extraction from the medium in which the microorganism are grown. For example, U.S. Pat. No. 5,595,887 describes methods of forming a variety of relatively small peptides through expression of a recombinant gene construct coding for a fusion protein which includes a binding protein and one or more copies of the desired target peptide. After expression, the fusion protein is isolated and cleaved using chemical and/or enzymatic methods to produce the desired target peptide.

The peptides used in the methods of the present invention may be employed in a monovalent state (i.e., free peptide or a single peptide fragment coupled to a carrier molecule). The peptides may also be employed as conjugates having more than one (same or different) peptide fragment bound to a single carrier molecule. The carrier may be a biological carrier molecule (e.g., a glycosaminoglycan, a proteoglycan, albumin or the like) or a synthetic polymer (e.g., a polyalkyleneglycol or a synthetic chromatography support). Typically, ovalbumin, human serum albumin, other proteins, polyethylene glycol, or the like are employed as the carrier. Such modifications may increase the apparent affinity and/or change the stability of a peptide. The number of peptide fragments associated with or bound to each carrier can vary, but from about 4 to 8 peptides per carrier molecule are typically obtained under standard coupling conditions.

For instance, peptide/carrier molecule conjugates may be prepared by treating a mixture of peptides and carrier molecules with a coupling agent, such as a carbodiimide. The coupling agent may activate a carboxyl group on either the peptide or the carrier molecule so that the carboxyl group can react with a nucleophile (e.g., an amino or hydroxyl group) on the other member of the peptide/carrier molecule, resulting in the covalent linkage of the peptide and the carrier molecule. For example, conjugates of a peptide coupled to ovalbumin may be prepared by dissolving equal amounts of lyophilized peptide and ovalbumin in a small volume of water. In a second tube, 1-ethyl-3-(3-dimethylamino-propyl)-carbodiimide hydrochloride (EDC; ten times the amount of peptide) is dissolved in a small amount of water. The EDC solution was added to the peptide/ovalbumin mixture and allowed to react for a number of hours. The mixture may then dialyzed (e.g., into phosphate buffered saline) to obtain a purified solution of peptide/ovalbumin conjugate. Peptide/carrier molecule conjugates prepared by this method typically contain about 4 to 5 peptides per ovalbumin molecule.

The present invention also provides a composition that includes one or more active agents (i.e., colostrinin, at least one constituent peptide thereof, or active analog thereof) of the invention and one or more carriers, preferably a pharmaceutically acceptable carrier. The methods of the invention include administering to, or applying to the skin of, a patient, preferably a mammal, and more preferably a human, a composition of the invention in an amount effective to produce the desired effect. The active agents of the present invention are formulated for enteral administration (oral, rectal, etc.) or parenteral administration (injection, internal pump, etc.). The administration can be via direct injection into tissue, interarterial injection, intervenous injection, or other internal administration procedures, such as through the use of an implanted pump, or via contacting the composition with a mucus membrane in a carrier designed to facilitate transmission of the composition across the mucus membrane such as a suppository, eye drops, inhaler, or other similar administration method or via oral administration in the form of a syrup, a liquid, a pill, capsule, gel coated tablet, or other similar oral administration method. The active agents can be incorporated into an adhesive plaster, a patch, a gum, and the like, or it can be encapsulated or incorporated into a bioerodible matrix for controlled release.

The carriers for internal administration can be any carriers commonly used to facilitate the internal administration of compositions such as plasma, sterile saline solution, IV solutions or the like. Carriers for administration through mucus membranes can be any well-known in the art. Carriers for administration oral can be any carrier well-known in the art.

The formulations may be conveniently presented in unit dosage form and may be prepared by any of the methods well known in the art of pharmacy. All methods include the step of bringing the active agent into association with a carrier which constitutes one or more accessory ingredients. In general, the formulations are prepared by uniformly and intimately bringing the active agent into association with a liquid carrier, a finely divided solid carrier, or both, and then, if necessary, shaping the product into the desired formulations.

Formulations suitable for parenteral administration conveniently include a sterile aqueous preparation of the active agent, or dispersions of sterile powders of the active agent, which are preferably isotonic with the blood of the recipient. Isotonic agents that can be included in the liquid preparation include sugars, buffers, and sodium chloride. Solutions of the active agent can be prepared in water, optionally mixed with a nontoxic surfactant. Dispersions of the active agent can be prepared in water, ethanol, a polyol (such as glycerol, propylene glycol, liquid polyethylene glycols, and the like), vegetable oils, glycerol esters, and mixtures thereof. The ultimate dosage form is sterile, fluid, and stable under the conditions of manufacture and storage. The necessary fluidity can be achieved, for example, by using liposomes, by employing the appropriate particle size in the case of dispersions, or by using surfactants. Sterilization of a liquid preparation can be achieved by any convenient method that preserves the bioactivity of the active agent, preferably by filter sterilization. Preferred methods for preparing powders include vacuum drying and freeze drying of the sterile injectible solutions. Subsequent microbial contamination can be prevented using various antimicrobial agents, for example, antibacterial, antiviral and antifungal agents including parabens, chlorobutanol, phenol, sorbic acid, thimerosal, and the like. Absorption of the active agents over a prolonged period can be achieved by including agents for delaying, for example, aluminum monostearate and gelatin.

Formulations of the present invention suitable for oral administration may be presented as discrete units such as tablets, troches, capsules, lozenges, wafers, or cachets, each containing a predetermined amount of the active agent as a powder or granules, as liposomes containing the active agent, or as a solution or suspension in an aqueous liquor or non-aqueous liquid such as a syrup, an elixir, an emulsion, or a draught. The amount of active agent is such that the dosage level will be effective to produce the desired result in the subject.

Nasal spray formulations include purified aqueous solutions of the active agent with preservative agents and isotonic agents. Such formulations are preferably adjusted to a pH and isotonic state compatible with the nasal mucous membranes. Formulations for rectal or vaginal administration may be presented as a suppository with a suitable carrier such as cocoa butter, or hydrogenated fats or hydrogenated fatty carboxylic acids. Ophthalmic formulations are prepared by a similar method to the nasal spray, except that the pH and isotonic factors are preferably adjusted to match that of the eye. Topical formulations include the active agent dissolved or suspended in one or more media such as mineral oil, DMSO, polyhydroxy alcohols, or other bases used for topical pharmaceutical formulations.

Useful dosages of the active agents can be determined by comparing their in vitro activity and the in vivo activity in animal models. Methods for extrapolation of effective dosages in mice, and other animals, to humans are known in the art; for example, see U.S. Pat. No. 4,938,949.

The tablets, troches, pills, capsules, and the like may also contain one or more of the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, fructose, lactose or aspartame; and a natural or artificial flavoring agent. When the unit dosage form is a capsule, it may further contain a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, or sugar and the like. A syrup or elixir may contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The active agent may be incorporated into sustained-release preparations and devices.

EXAMPLES

The invention will be further described by reference to the following detailed examples. The examples are meant to provide illustration and should not be construed as limiting the scope of the present invention.

Materials and Methods

Preparation of Peptides:
1. Wash pre-loaded resin with DMF (dimethylformamide), then drain completely.
2. Add 10 ml of 20% piperidine/DMF to resin. Shake for 5 minutes, then drain.
3. Add another 10 ml of 20% piperidine/DMF. Shake for 30 minutes.
4. Drain reaction vessel and wash resin with DMF four times. Then wash once with DCM (dichloromethanol). Check beads using the ninhydrin test—the beads should be blue.
5. The coupling step was carried out as follows:
   a. Prepare the following solution: 1 mmole Fmoc (i.e. fluorenylmethyloxycarbonyl) amino acid 2.1 ml of 0.45 M HBTU/HOBT (1 mmol) (2-(1H-benzotriazol-1-yl)-1,1,3,3-tetramethyluronium hexafluorophosphate/N-hydroxybenzotriazole-$H_2O$) 348 µl of DIEA (2 mmol) (diisopropylethylamine); and
   b. Add the solution to the resin and shake for a minimum of 30 minutes.
6. Drain reaction vessel and wash the resin again with DMF four times and with DCM once.
7. Perform the ninhydrin test: If positive (no colour)— proceed to step 2 and continue synthesis; If negative (blue colour)— return to step 5 and recouple the same Fmoc amino acid.
8. After the synthesis was complete, the peptide was cleaved from the resin with 5% $H_2O$, 5% phenol, 3% Thionisole, 3% EDT (ethanedithiol), 3% triisopropylsilane and 81% TFA for 2 hours.
9. After 2 hours, filter into cold MTBE (methyl t-butyl ether). The precipitated peptide was then washed twice with cold MTBE and dried under nitrogen gas.
10. The molecular weight of the synthesised peptides was checked by Matrix-Assisted Laser Desorption Time-of-Flight Mass Spectroscopy (LDMS), and the purity was checked by HPLC using a C-18, 300 Angstrom, 5 µm column.

Cells: PC12 cell line derived from medullary pheochromocytoma cells were used to undertake studies described bellow. PC 12 cells were obtained from the American Type Culture Collection and maintained in RPMI-1640 supplemented with 10% fetal bovine serum (HYCLONE Inc), penicillin (100 U/ml) and streptomycin (100 µg/ml).

Methods: To evaluate the effect of colostrum, colostrinin and its component peptides on cell differentiation $3 \times 10^4$ logarithmically replicating (70% confluence) PC12 cells were seeded in 24× well plates and cells were allowed to adhere and grow for 24 hours. Serum containing media were aspirated and replaced for serum-free RPMI containing appropriate amount of antibiotics. In four parallel, increasing concentrations (0.1, 1, 10 and 100 µg per ml) of colostrum, colostrinin and its component peptides were added directly into the media and incubated at 37° C. As a positive control, nerve growth factor (NGF) 7S (Gibco-BRL) was used at 100 ng per ml concentration (Chao, Cell, 69, 995–997 (1992); and Marshall et al., Cell 80, 179–185 (1995)). Phorbol 12-myristate 13-acetate (TPA: 10 ng per ml) was used as a negative control. Eight hours later the media were changed and RPMI-1640 was added containing 1% or 10% fetal bovine serum. The cultures were microscopically investigated $2^{nd}$, $4^{th}$ and $6^{th}$ days after treatment. Six days after treatment cells were fixed with paraformaldehyde (4%) and stained with 0.01% crystal violet solution. Excess of dyes were removed by ethanol washing. The final evaluation took place using a microscopy (Axiophot2 Zeiss Inc., Germany).

Results

Control non-treated cells demonstrated the usual rounded morphology, continued to replicate and reach 70% to 80% confluency during 7 days experimental period. The mock-treated control and TPA exposed cells showed a low background level of differentiation (less than 0.01%). In the assay system used herein, NGF (100 ng per ml) mediated a cell cycle arrest as previously described (Chao, Cell, 68, 995–997 (1992)). In several experiments, in the presence of 10% fetal bovine serum NGF-mediated an induction of cell differentiation that observed in 45±11% of cells. When cells were subjected to NGF-mediated differentiation in the presence of 1% serum 5% to 10% of cells showed morphological changes. The differentiated cells showed typical neuron-like morphology. In parallel experiments, nine component peptides, colostrinin and colostrum were tested. The results are summarized in Table 1.

In the presence of 1% fetal bovine serum there was no cell differentiation observed. These data indicate that some of the serum factor(s) are required to biological effect of these compounds. On the other hand, in the presence of 10% serum, the component peptides, colostrinin as well as colostrum have induced cell differentiation in PC12 cells. The morphological changes (fibroblast-like, epitheloid, neuron-like) are shown in FIG. 1. These data are in agreement with cytokine inducing activity of these peptides. For example, IFN-gamma and nerve growth factor was shown to induce similar signal transduction cascades (Peunova et al., Nature, 375, 68–73 (1995)).

TABLE 1

Effect of colostrum, colostrinin, and its component peptides on morphology (differentiation) of medullary pheochromocytoma (PC12) cells.

| Peptide | Concentration µg/ml | 1% FBS | 10% FBS | Cell morphology |
|---|---|---|---|---|
| SEQ ID NO:1 | 100 | − | +/− | epitheloid |
|  | 10 | − | ++ | neuron-like |
|  | 1.0 | − | + |  |
|  | 0.1 | − | +/− |  |
| SEQ ID NO:7 | 100 | − | +/− | fibroblast-like |
|  | 10 | − | + | neuron-like |
|  | 1.0 | − | + |  |
|  | 0.1 | − | − |  |
| SEQ ID NO:8 | 100 | − | − | fibroblast-like |
|  | 10 | − | + | neuron-like |
|  | 1.0 | − | ++ |  |
|  | 0.1 | − | − |  |
| SEQ ID NO:3 | 100 | − | + | fibroblast-like |
|  | 10 | − | + | neuron-like |
|  | 1.0 | − | +/− |  |
|  | 0.1 | − | − |  |
| SEQ ID NO:2 | 100 | − | + | fibroblast-like |
|  | 10 | + | ++ | neuron-like |
|  | 1.0 | − | ++ |  |
|  | 0.1 | − | +/− |  |
| SEQ ID NO:4 | 100 | − | ++ | fibroblast-like |
|  | 10 | − | ++ | epitheloid |
|  | 1.0 | − | + | neuron-like |
|  | 0.1 | − | − |  |
| SEQ ID NO:5 | 100 | − | + | fibroblast-like |
|  | 10 | − | +/− | epitheloid |
|  | 1.0 | − | − | neuron-like |
|  | 0.1 | − | − |  |
| SEQ ID NO:6* | 100 | − | + | fibroblast-like |
|  | 10 | − | + | epitheloid |
|  | 1.0 | − | +/− |  |
|  | 0.1 | − | − |  |
| SEQ ID NO:31 | 100 | NT | NT | fibroblast-like |
|  | 10 | − | +/− | neuron-like |
|  | 1.0 | − |  |  |
|  | 0.1 |  | − |  |
| Colostrinin | 100 | NT | NT | fibroblast-like |
|  | 10 | + | ++ | neuron-like |
|  | 1.0 | − | ++ |  |
|  | 0.1 |  | − |  |
| Colostrum | 100 | NT | NT | fibroblast-like |
|  | 10 | − | ++ | neuron-like |
|  | 1.0 | − | ++ |  |
|  | 0.1 | − | +/− |  |
| NGF | 0.1 | ++++ | ++++ | neuron-like |
| TPA (Negative Control) | 0.1 |  |  | rounded |
| Control | — | − | − | rounded |

NT = Not Tested; − = ≤0.01% (back-ground); + = 1%; ++ = 1–5%; +++ = 6–15%; ++++ = >15%
*Although the cells treated with SEQ ID NO:6 did not show neuron-like cell morphology upon visual inspection, additional tests are needed to definitively prove such morphology changes did not occur.

Although the invention has been disclosed with reference to its preferred embodiments, from reading this description those of skill in the art may appreciate changes and modification that may be made which do not depart from the scope and spirit of the invention as described above and claimed hereafter. All references, patents, and patent applications cited herein are incorporated herein by reference in their entirety as if individually incorporated.

| SEQ ID NO:1 | MQPPPLP |
|---|---|
| SEQ ID NO:2 | LQTPQPLLQVMMEPQGD |
| SEQ ID NO:3 | DQPPDVEKPDLQPFQVQS |
| SEQ ID NO:4 | LFFFLPVVNVLP |
| SEQ ID NO:5 | DLEMPVLPVEPFPFV |
| SEQ ID NO:6 | MPQNFYKLPQM |
| SEQ ID NO:7 | VLEMKFPPPPQETVT |
| SEQ ID NO:8 | LKPFPKLKVEVFPFP |
| SEQ ID NO:9 | VVMEV |
| SEQ ID NO:10 | SEQP |
| SEQ ID NO:11 | DKE |
| SEQ ID NO:12 | FPPPK |
| SEQ ID NO:13 | DSQPPV |
| SEQ ID NO:14 | DPPPPQS |
| SEQ ID NO:15 | SEEMP |
| SEQ ID NO:16 | KYKLQPE |
| SEQ ID NO:17 | VLPPNVG |
| SEQ ID NO:18 | VYPFTGPIPN |
| SEQ ID NO:19 | SLPQNILPL |
| SEQ ID NO:20 | TQTPVVVPPF |
| SEQ ID NO:21 | LQPEIMGVPKVKETMVPK |
| SEQ ID NO:22 | HKEMPFPKYPVEPFTESQ |
| SEQ ID NO:23 | SLTLTDVEKLHLPLPLVQ |
| SEQ ID NO:24 | SWMHQPP |
| SEQ ID NO:25 | QPLPPTVMFP |
| SEQ ID NO:26 | PQSVLS |
| SEQ ID NO:27 | LSQPKVLPVPQKAVPQRDMPIQ |
| SEQ ID NO:28 | AFLLYQE |
| SEQ ID NO:29 | RGPFPILV |
| SEQ ID NO:30 | ATFNRYQDDHGEEILKSL |
| SEQ ID NO:31 | VESYVPLFP |
| SEQ ID NO:32 | FLLYQEPVLGPVR |
| SEQ ID NO:33 | LNF |
| SEQ ID NO:34 | MHQPPQPLPPTVMFP |

We claim:

1. A method for promoting cell differentiation, the method comprising contacting pluripotent cells effective to form neuronal cells with a neuronal cell regulator selected from the group consisting of colostrinin, a constituent peptide of colostrinin, an active analog of a constituent peptide of colostrinin, and combinations thereof, under conditions effective to change pluripotent cells in morphology to form neuronal cells;

wherein the constituent peptide of colostrinin is selected from the group consisting of MQPPPLP (SEQ ID NO:1), LQTPQPLLQVMMEPQGD (SEQ ID NO:2), DQPPDVEKPDLQPFQVQS (SEQ ID KO:3), LFF-FLPVGVLP (SEQ ID NO:4), DLEMPVLPVEPFPFV (SEQ ID NO: 5), MPQNFYKLPQM (SEQ ID NO:6), VLEMKFPPPPQETVT (SEQ ID NO:7), LKPFPCK-VEVFPFP (SEQ ID NO:8), VESYVPLFP (SEQ ID NO:31), MHQPPQPLPPTVMFP (SEQ ID NO:34), and combinations thereof;

wherein an active analog of a constituent peptide of colostrinin comprises a peptide having an amino acid sequence with at least about 15 percent proline and having at least about 70 percent sequence identity to a constituent peptide of colostrinin selected from the group consisting of MQPPPLP (SEQ ID NO:1), LQT-PQPLLQVMMEPQGD (SEQ ID NO:2), DQPPD-VEKPDLQPFQVQS (SEQ ID KO:3), LFF-FLPVGVLP (SEQ ID NO:4), DLEMPVLPVEPFPFV (SEQ ID NO:5), MPQNFYKLPQM (SEQ ID NO:6), VLEMKFPPPPQETVT (SEQ ID NO:7), LKPFPCK-VEVFPFP (SEQ ID NO: 8), VESYVPLFP (SEQ ID NO:31), and MHJQPPQPLPPTVMPP (SEQ ID NO:34);

and wherein said pluripotent cells change in morphology to form neuronal cells.

2. The method of claim 1 wherein the cells are present in a cell culture, an organ, a tissue, or an organism.

3. The method of claim 1 wherein the cells are mammalian cells.

4. The method of claim 3 wherein the cells are human cells.

5. The method of claim 1 wherein the neuronal cell regulator is a constituent peptide of colostrinin or an active analog of a constituent peptide of colostrinin.

6. The method of claim 1 wherein the neuronal cell regulator is selected from the group consisting of MQPPPLP (SEQ ID NO:1), LQTPQPLLQVMMEPQGC (SEQ ID NO:2), DQPPDVEKPDLQPFQVQS (SEQ ID KO:3), LFFLPVGVLP (SEQ ID NO:4), DLEMPVLPVEPFPFV (SEQ ID NO:5), MPQNFYKLPQM (SEQ ID NO:6), VLEMKFPPPPQETVT (SEQ ID NO:7), LKPFPCKVEVF-PFP (SEQ ID NO:8), VESYVPLFP (SEQ ID NO:31), and MHQPPQPLPPTVMFP (SEQ ID NO:34), and combinations thereof.

7. The method of claim 6 wherein the neuronal cell regulator is selected from the group consisting of MQPPPLP (SEQ ID NO:1), LQTPQPLLQVMMEPQGD (SEQ ID NO:2), DQPPDVEUDLQPFQVQS (SEQ ID NO:3), LFF-FLPVVNVLP (SEQ ID NO: 4), DLEMPVLPVEPFPFV (SEQ ID NO: 5), MPQNFYKLPQM (SEQ ID NO: 6), VLEMKFPPPPQEWT (SEQ ID NO:7), LKPFP-KLKVEVFPFP (SEQ ID NO:8), and combinations thereof.

8. A method for promoting neuronal cell differentiation in a patient, the method comprising administering to the patient a neuronal cell regulator selected from the group consisting of colostrinin, a constituent peptide of colostrinin, an active analog of a constituent peptide of colostrinin, and combinations thereof, under conditions effective to promote differentiation of pluripotent cells to form neuronal cells;

wherein the constituent peptide of colostrinin is selected from the group consisting of MQPPPLP (SEQ ID NO:1), LQTPQPLLQVMMEPQGD (SEQ ID NO:2), DQPPDVEKPDLQPFQVQS (SEQ ID KO:3), LFF-FLPVGVLP (SEQ ID NO:4), DLEMPVLPVEPFPFV (SEQ ID NO:5), MPQNFYKLPQM (SEQ ID NO:6), VLEMKFPPPPQETVT (SEQ ID NO:7), LKPFPCK-VEVFPFP (SEQ ID NO:8), VESYVPLFP (SEQ ID NO:31), and MHQPPQPLPPTVMFP (SEQ ID NO:34);

wherein an active analog of a constituent peptide of colostrinin comprises a peptide having an amino acid sequence with at least about 15 percent proline and having at least about 70 percent sequence identity to a constituent peptide of colostrinin selected from the group consisting of MQPPPLP (SEQ ID NO:1), LQT-PQPLLQVMMEPQGD (SEQ ID NO:2), DQPPD-VEKPDLQPFQVQS (SEQ ID KO:3), LFF-FLPVGVLP (SEQ ID NO:4), DLEMPVLPVEPFPFV (SEQ ID NO:5), MPQNFYKLPQM (SEQ ID NO:6), VLEMKFPPPPQETVT (SEQ ID NO:7), LKPFPCK-VEVFPFP (SEQ ID NO:8), VESYVPLFP (SEQ ID NO:31), and MHQPPQPLPPTVMFP (SEQ ID NO:34);

and wherein said pluripotent cells differentiate to form neuronal cells.

9. The method of claim 8 wherein the patient is human.

10. The method of claim 8 wherein the neuronal cell regulator is a constituent peptide of colostrinin or an active analog of a constituent peptide of colostrinin.

11. The method of claim 8 wherein the neuronal cell regulator is selected from the group consisting of MQPPPLP (SEQ ID NO:1), LQTPQPLLQVMMEPQGD (SEQ ID NO:2), DQPPDVEKPDLQPFQVQS (SEQ ID KO:3), LFF-FLPVGVLP (SEQ ID NO:4), DLEMPVLPVEPFPFV (SEQ ID NO:5), MPQNFYKLPQM (SEQ ID NO:6), VLEMKF-PPPPQETVT (SEQ ID NO:7), LKPFPCKVEVFPFP (SEQ ID NO:8), VESYVPLFP (SEQ ID NO:31), MHQPPQ-PLPPTVMFP (SEQ ID NO:34), and combinations thereof.

12. The method of claim 11 wherein the neuronal cell regulator is selected from the group consisting of MQPPPLP (SEQ ID NO:1), LQTPQPLLQVMMEPQGD (SEQ ID NO:2), DQPPDVEKPDLQPFQVQS (SEQ ID NO:3), LFFFLPVGVLP (SEQ ID NO:4), DLEMPVLPVEPFPFV (SEQ ID NO:5), MPQNFYKLPQM (SEQ ID NO:6), VLEMKFPPPPQETVT (SEQ ID NO:7), LKPFPKLKVEVFPFP (SEQ ID NO: 8), and combinations thereof.

13. A method for promoting neuronal cell differentiation, the method comprising contacting pluripotent cells of the nervous system with a neuronal cell regulator selected from the group consisting of colostrinin, a constituent peptide of colostrinin, an active analog of a constituent peptide of colostrinin, and combinations thereof, under conditions effective to promote differentiation of pluripotent cells to form neuronal cells;

wherein the constituent peptide of colostrinin is selected from the group consisting of MQPPPLP (SEQ ID NO:1), LQTPQPLLQVMMEPQGD (SEQ ID NO:2), DQPPDVEKPDLQPFQVQS (SEQ ID KO:3), LFFFLPVGVLP (SEQ ID NO:4), DLEMPVLPVEPFPFV (SEQ ID NO:5), MPQNFYKLPQM (SEQ ID NO:6), VLEMKFPPPPQETVT (SEQ ID NO:7), LKPFPCKVEVFPFP (SEQ ID NO: 8), VESYVPLFP (SEQ ID NO:31), and MHQPPQPLPPTVMFP (SEQ ID NO:34);

wherein an active analog of a constituent peptide of colostrinin comprises a peptide having an amino acid sequence with at least about 15 percent proline and having at least about 70 percent sequence identity to a constituent peptide of colostrinin selected from the group consisting of MQPPPLP (SEQ ID NO:1), LQTPQPLLQVMMEPQGD (SEQ ID NO:2), DQPPDVEKPDLQPFQVQS (SEQ ID KO:3), LFFFLPVGVLP (SEQ ID NO:4), DLEMPVLPVEPFPFV (SEQ ID NO:5), MPQNFYKLPQM (SEQ ID NO:6), VLEMKFPPPPQETVT (SEQ ID NO:7), LKPFPCKVEVFPFP (SEQ ID NO:8), VESYVPLFP (SEQ ID NO:31), and MHQPPQPLPPTVMFP (SEQ ID NO:34).

14. The method of claim 13 wherein the cells are present in a cell culture, an organ, a tissue, or an organism.

15. The method of claim 13 wherein the cells are mammalian cells.

16. The method of claim 15 wherein the cells are human cells.

17. The method of claim 13 wherein the neuronal cell regulator is a constituent peptide of colostrinin or an active analog of a constituent peptide of colostrinin.

18. The method of claim 14 wherein the neuronal cell regulator is selected from the group consisting of MQPPPLP (SEQ ID NO:1), LQTPQPLLQVMMEPQGD (SEQ ID NO:2), DQPPDVEKPDLQPFQVQS (SEQ ID KO:3), LFFFLPVGVLP (SEQ ID NO:4), DLEMPVLPVEPFPIFV (SEQ ID NO:5), MPQNFYKLPQM (SEQ ID NO:6), VLEMKFPPPPQETVT (SEQ ID NO:7), LKPFPCKVEVFPFP (SEQ ID NO: 8), VESYVPLFP (SEQ ID NO:31), MHQPPQPLPPTVMFP (SEQ ID NO:34), and combinations thereof.

19. The method of claim 14 wherein the neuronal cell regulator is selected from the group consisting of MQPPPLP (SEQ ID NO:1), LQTPQPLLQVMMEPQGD (SEQ ID NO:2), DQPPDVEKPDLQPFQVQS (SEQ ID NO:3), LFFFLPVGVLP (SEQ ID NO:4), DLEMPVLPVEPFPFV (SEQ ID NO:5), MPQNFYKLPQM (SEQ ID NO:6), VLEMKFPPPPQETVT (SEQ ID NO: 7), LKPFPKLKVEVFPFP (SEQ ID NO:8), and combinations thereof.

20. A method for promoting neuronal cell differentiation in a patient, the method comprising administering to the patient a neuronal cell regulator selected from the group consisting of colostrinin, a constituent peptide of colostrinin, an active analog of a constituent peptide of colostrinin, and combinations thereof, under conditions effective to promote differentiation of pluripotent cells of the nervous system to form neuronal cells;

wherein the constituent peptide of colostrinin is selected from the group consisting of MQPPPLP (SEQ ID NO:1), LQTPQPLLQVMMEPQGD (SEQ ID NO:2), DQPPDVEKPDLQPFQVQS (SEQ ID KO:3), LFFFLPVGVLP (SEQ ID NO:4), DLEMPVLPVEPFPFV (SEQ ID NO:5), MPQNFYKLPQM (SEQ ID NO:6), VLEMKFPPPPQETVT (SEQ ID NO:7), LKPFPCKVEVFPFP (SEQ ID NO:8), VESYVPLFP (SEQ ID NO:31), and MHQPPQPLPPTVMFP (SEQ ID NO:34);

wherein an active analog of a constituent peptide of colostrinin comprises a peptide having an amino acid sequence with at least about 15 percent proline and having at least about 70 percent sequence identity to a constituent peptide of colostrinin selected from the group consisting of MQPPPLP (SEQ ID NO:1), LQTPQPLLQVMMEPQGD (SEQ ID NO:2), DQPPDVEKPDLQPFQVQS (SEQ ID KO:3), LFFFLPVGVLP (SEQ ID NO:4), DLEMPVLPVEPFPFV (SEQ ID NO: 5), MPQNFYKLPQM (SEQ ID NO:6), VLEMKFPPPPQETVT (SEQ ID NO:7), LKPFPCKVEVFPFP (SEQ ID NO:8), VESYVPLFP (SEQ ID NO:31), and MIIQPPQPLPPTVMFP (SEQ ID NO: 34);

and wherein pluripotent cells of the nervous system differentiate to form neuronal cells.

21. The method of claim 20, wherein the patient is human.

22. The method of claim 20 wherein the neuronal cell regulator is a constituent peptide of colostrinin or an active analog of a constituent peptide of colostrinin.

23. The method of claim 20 wherein the neuronal cell regulator is selected from the group consisting of MQPPPLP (SEQ ID NO:1), LQTPQPLLQVMMEPQGD (SEQ ID NO:2), DQPPDVEKYDLQPFQVQS (SEQ ID KO:3), LFFFLPVGVLP (SEQ ID NO:4), DLEMPVLPVEPFPFV (SEQ ID NO:5), MPQNFYKLPQM (SEQ ID NO:6), VLEMKFPPPPQETVT (SEQ ID NO:7), LKPFPCKVEVFPFP (SEQ ID NO:8), VESYVPLFP (SEQ ID NO:31), MHQPPQPLPPTVMFP (SEQ ID NO:34), and combinations thereof.

24. The method of claim 20 wherein the neuronal cell regulator is selected from the group consisting of MQPPPLP (SEQ ID NO:1), LQTPQPLLQVMMEPQGD (SEQ ID NO:2), DQPPDVEKPDLQPFQVQS (SEQ ID NO:3), LFFFLPVGVLP (SEQ ID NO:4), DLEMPVLPVEPFPFV (SEQ ID NO:5), MPQNFYKLPQM (SEQ ID NO: 6), VLEMKFPPPPQETVT (SEQ ID NO:7), LKPFPKLKVEVFPFP (SEQ ID NO:8), and combinations thereof.

* * * * *

UNITED STATES PATENT AND TRADEMARK OFFICE
CERTIFICATE OF CORRECTION

| | | |
|---|---|---|
| PATENT NO. | : 6,852,685 B1 | |
| APPLICATION NO. | : 09/641802 | |
| DATED | : February 8, 2005 | |
| INVENTOR(S) | : Boldogh et al. | |

It is certified that error appears in the above-identified patent and that said Letters Patent is hereby corrected as shown below:

On the title page, item (56) References Cited, under "U.S. Patent Documents," please add the following document:
--US 2003/0091606 A1    05/15/03    Stanton et al.--;

On the title page, under "Foreign Patent Documents," please add the following documents:
--WO 95/00155    01/05/95--;
--WO 02/13849    02/21/02--;
--WO 02/13850    02/21/02--;
--WO 02/13851    02/21/02--;

On the title page item (56) References Cited, under "Other Publications," Second Column, please delete "Janusz et al. (1987) mmunoregulatory Properties of Synthetic" and insert --Janusz et al. (1987) Immunoregulatory Properties of Synthetic--

On the title page, under "Other Publications," second column, please delete "Inglot, Junsz, and Lisowski" and insert --Inglot, Janusz, and Lisowski--

On the title page, under "Other Publications," please add the following publications:
--Boldogh et al., "Modulation of 4HNE-Mediated Signaling by proline-rich peptides from Ovine Colostrum," *J Mol Neuroscience*, May 2003;20(2): 125-134.--;

--Brown et al., "7-Hydroperoxycholesterol and its products in oxidized low density lipoprotein and human atherosclerotic plaque," *J. Lipid Res,* 1997;38: 1730-1745.--;

--Bruce-Keller et al., "4-Hydroxynonenal, a product of lipid peroxidation, damages cholinergic neurons and impairs visuospatial memory in rats," *J Neuropathol Exp Neurol*, 1998:57: 257-267.--;

--Buettner, G.R., "The pecking order of free radicals and antioxidants: lipid peroxidation, alpha-tocopherol, and ascorbate," *Arch Biochem Biophys*, 1993;300: 535-543.--;

--Cadenas et al., "Mitochondrial free radical generation, oxidative stress, and aging," *Free Radic Biol Med*, 2000;29:222-230.--;

--Camandola et al., "The lipid peroxidation product 4-hydroxy-2,3-nonenal inhibits constitutive and inducible activity of nuclear factor kappa B in neurons," *Brain Res Mol Brain Res*, 2000;85:53-60.--;

UNITED STATES PATENT AND TRADEMARK OFFICE
CERTIFICATE OF CORRECTION

PATENT NO. : 6,852,685 B1
APPLICATION NO. : 09/641802
DATED : February 8, 2005
INVENTOR(S) : Boldogh et al.

It is certified that error appears in the above-identified patent and that said Letters Patent is hereby corrected as shown below:

--Cheng et al., "Effect on mGST A4 transfection on 4-hydroxynonenal-mediated apoptosis and differentiation of K562 human erythroleukemia cells," *Arch Biochem Biophys*, 1999;372: 29-36.--;

--Davies et al., "Photo-oxidation of proteins and its role in cataractogenesis," *J. Photochem. Photobiol B*, 2001;63: 114-125.--;

--Davis et al., "Cellular thiols and reactive oxygen species in drug-induced apoptosis," *J. Pharmacol Exp Ther*, 2001;296: 1-6.--;

--DeZwart et al., "Biomarkers of free radical damage applications in experimental animals and in humans," *Free Radic Biol Med*, 1999; 26:202-226.--;

--Evan et al., "A matter of life and cell death," *Science*, 1998; 281: 1317-1322.--;

--Finkel et al., "Oxidants, oxidative stress and the biology of ageing," *Science*, 1998;281: 1317-1322.--;

--Friguet et al., "Protein degradation by the proteasome and its implications in aging," *Ann N Y Acad Sci*, 2000;908: 143-154.--;

--Gardner et al., "Development of a peptide antibody specific to human glutathione S-transferase alpha 4-4 (hGSTA4-4) reveals preferential localization in human liver mitochondria," *Arch Biochem Biophys*, 2001;390: 19-27.--;

--Hainut et al., "Redox modulation of p53 conformation and sequence-specific DNA binding in vitro," *Cancer Res*, 1993;53: 4469-4473.--;

--Han et al., "Implication of a small GTPase Rac1 in the activation of c-Jun-N-terminal kinase and heat shock factor in response to heat shock," *J Biol Chem*, 2001; 276:1889-1895.--;

--Hughes et al., "Mediation of nerve growth factor-driven cell cycle arrest in PC12 cells by p53. Simultaneous differentiation and proliferation subsequent to p53 functional inactivation," *J Biol Chem*, 2000;275: 37829-37837.--;

--Janusz et al., "Immunoregulatory properties of synthetic peptides, fragments of a proline-rich polypeptide (PRP) from ovine colostrum," *Molecular Immunology*, October 1987;24(10): 1029-1031.--;

UNITED STATES PATENT AND TRADEMARK OFFICE
CERTIFICATE OF CORRECTION

PATENT NO. : 6,852,685 B1
APPLICATION NO. : 09/641802
DATED : February 8, 2005
INVENTOR(S) : Boldogh et al.

It is certified that error appears in the above-identified patent and that said Letters Patent is hereby corrected as shown below:

--Keller et al., "Mitochondrial manganese superoxide dismutase prevents neural apoptosis and reduces ischemic brain injury: suppression of peroxynitrite production, lipid peroxidation, and mitochondrial dysfunction," *J Neurosci*, 1998;18: 687-697.--;

--Kong et al., "Signal transduction events elicited by natural products: a role of MAPK and caspase pathways in homeostatic response and induction of apoptosis," *Arch Pharm Res*, 2000;23: 1-16.--;

--Kruman et al., "Evidence that 4-hydroxynonenal mediates oxidative stress-induced neuronal apoptosis," *J Neurosci*, 1997;17:5089-5100.--;

--Lafon-Cazal et al., "Nitric oxide, superoxide and peroxynitrite: putative mediators of NMDA-induced cell death in cerebellar granule cells," *Neuropharmacology*, 1993;32: 1259-1266.--;

--Leonarduzzi et al., "Lipid oxidation products in cell signaling," *Free Radic Biol Med*, 2000;28: 1370-1378.--;

--Ley et al., "Adhesion Molecules in Lymphocyte Trafficking and Colitis," *Gastroenterology*, October 2001;121(4);Editorial:1008-1010.--;

--Mattson et al., "Alzheimer's disease. Short Precursor shortens memory," *Nature*, 1997;387: 457-458.--;

--Nakamura et al., "Redox regulation of cellular activation," *Annu Rev Immunol*, 1997;15: 351-369.--;

--Page et al., "4-Hydroxynonenal prevents NF-kappaB activation and tumor necrosis factor expression by inhibiting IkappaB phosphorylation and subsequent proteolysis," *J Biol Chem*, 1999; 274:11611-11618.--;

--Parola et al., "HNE interacts directly with JNK isoforms in human hepatic stellate cells," *J Clin Invest*, 1998;102:1942-1950.--;

--Perkins et al., "Association of antioxidants with memory in a multiethnic elderly sample using the Third National Health and Nutrition Examination Survey," *Am J Epidemiol*, 1999;150: 37-44.--;

--Perrig et al., "The relation between antioxidants and memory performance in the old and very old," *J Am Geriatr Soc*, 1997;45: 718-724.--;

UNITED STATES PATENT AND TRADEMARK OFFICE
CERTIFICATE OF CORRECTION

PATENT NO. : 6,852,685 B1
APPLICATION NO. : 09/641802
DATED : February 8, 2005
INVENTOR(S) : Boldogh et al.

It is certified that error appears in the above-identified patent and that said Letters Patent is hereby corrected as shown below:

--Poli et al., "4-Hydroxynonenal in the pathomechanisms of oxidative stress," *IUBMB Life*, 2000;50: 315-321.--;

--Rivas-Arancibia et al., "Effects of ozone exposure in rats on memory and levels of brain and pulmonary superoxide dismutase," *Environ Res*, 1998;76: 33-39.--;

--Ross et al., "Atherosclerosis: a cancer of the blood vessels?," *Am J Clin Pathol 116 Suppl*, 2001:S97-107.--;

--Rusnak et al., "Sensing electrons: protein phosphatase redox regulation," *Trends Biochem Sci*, 2000;25: 527-529.--;

--Salmi et al., "Immune Cell Trafficking in Uterus and Early Life is Dominated by the Mucosal Addressin MadCAM-1 in Humans," *Gastroenterology*, October 2001;121(4): 853-864.--;

--Sano et al., "A controlled trial of selegiline, alpha-tocopherol, or both as treatment for Alzheimer's disease," *The Alzeheimer's Disease Cooperative Study, N Engl J Med*, 1997;336:1216-1222.--;

--Sayre et al., "4-Hydroxynonenal-derived advanced lipid peroxidation end products are increased in Alzheimer's disease," *J Neurochem*, 1997;68: 2092-2097.--;

--Senft et al., "Determining glutathione and glutathione disulfide using the fluorescense probe o-phthaladehyde," *Anal Biochem*, 2000; 280: 80-86.--;

--Sinclair et al., "Altered plasma antioxidant status in subjects with Alzheimer's disease and vascular dementia," *Int J Geriatr Psychiatry*, 1998;13: 840-845.--;

--Uchida et al., "Modification of histidine residures in proteins by reaction with 4-hydroxynonenal," *Proc Natl Acad Sci USA*, 1992;89:4544-4548.--;

--Vaglini et al., "Cytochrome P450 and parkinsonism: protective role of CYP2E1," *Funct Neurol*, 2001;16: 107-112.--;

--Woods et al., "Regulation of p53 function," *Exp Cell Res*, 2001;264: 56-66.--;

--Yoritaka et al., "Immunohistochemical detection of 4-hydroxynonenal protein adducts in Parkinson disease," *Proc Natl Acad Sci USA*, 1996;93: 2696-2701.--;

UNITED STATES PATENT AND TRADEMARK OFFICE
CERTIFICATE OF CORRECTION

PATENT NO. : 6,852,685 B1
APPLICATION NO. : 09/641802
DATED : February 8, 2005
INVENTOR(S) : Boldogh et al.

It is certified that error appears in the above-identified patent and that said Letters Patent is hereby corrected as shown below:

--Zimecki et al., "Immunotropic properties of fractions isolated from human milk," *Arch Immunol Ther Exp*, 1984;32: 203-209.--;

--Zimecki et al., "The effect of a proline-rich polypeptide (PRP) on the humoral immune response. II. PRP induces differentiation of helper cells from glass-nonadherent thymocytes (NAT) and suppressor cells from glass-adherent thymocytes (GAT)," *Arch Immunol Ther Exp*, 1984;32: 197-201.--;

--Zimecki et al., "The effect of a poline-rich polypeptide (PRP) on the humoral immune response. I. Distinct effect of PRP on the T cell properties of mouse glass-nonadherent (NAT) and glass-adherent (GAT) thymocytes in thymectomized mice," *Arch Immunol Ther Exp*, 1984;32: 191-196.--.

Please replace Figure 1 with the formal drawing of Figure 1 which was filed February 20, 2001 and accepted by the Examiner in the Office Action mailed September 10, 2002.

In column 3, line 24, please delete "were treated with NGF or colostrinin," and insert --were treated with NGF or colostrum,--;

In column 4, line 54, please delete "LQTPQPLLQVMMEPQGC" and insert --LQTPQPLLQVMMEPQGD--;

In column 4, line 58, please delete "VLMKFPPPPQETVT" and insert --VLEMKFPPPPQETVT--;

In column 4, line 66, please delete "YKEMPFPKYPVEPFTESQ" and insert --HKEMPFPKYPVEPFTESQ--;

In column 25, line 26, please delete "(SEQ ID KO:3)" and insert --(SEQ ID NO:3)--;

In column 25, lines 26-27, please delete "LFFFLPVGVLP" and insert --LFFFLPVVNVLP--;

In column 25, lines 29-30, please delete "LKPFPCKVEVFPFP" and insert --LKPFPKLKVEVFPFP--;

In column 25, line 40, please delete "(SEQ ID KO:3)" and insert --(SEQ ID NO:3)--;

UNITED STATES PATENT AND TRADEMARK OFFICE
CERTIFICATE OF CORRECTION

PATENT NO.      : 6,852,685 B1
APPLICATION NO. : 09/641802
DATED           : February 8, 2005
INVENTOR(S)     : Boldogh et al.

It is certified that error appears in the above-identified patent and that said Letters Patent is hereby corrected as shown below:

In column 25, lines 40-41, please delete "LFFFLPVGVLP" and insert --LFFFLPVVNVLP--;

In column 25, lines 43-44, please delete "LKPFPCKVEVFPFP" and insert --LKPFPKLKVEVFPFP--;

In column 25, line 45, please delete "MHJQPPQPLPPTVMPP" and insert --MHQPPQPLPPTVMFP--;

In column 25, line 60, please delete "LQTPQPLLQVMMEPQGC" and insert --LQTPQPLLQVMMEPQGD--;

In column 25, line 61, please delete "(SEQ ID KO:3)" and insert --(SEQ ID NO:3)--;

In column 25, line 62, please delete "LFFLPVGVLP" and insert --LFFFLPVVNVLP--;

In column 25, lines 64-65, please delete "LKPFPCKVEVFPFP" and insert --LKPFPKLKVEVFPFP--;

In column 26, line 17, please delete "DQPPDVEUDLQPFQVQS" and insert --DQPPDVEKPDLQPFQVQS--;

In column 26, line 20, please delete "VLEMKFPPPPQEWT" and insert --VLEMKFPPPPQETVT--;

In column 26, line 32, please delete "(SEQ ID KO:3)" and insert --(SEQ ID NO:3)--;

In column 26, lines 32-33, please delete "LFFFLPVGVLP" and insert --LFFFLPVVNVLP--;

In column 26, lines 35-36, please delete "LKPFPCKVEVFPFP" and insert --LKPFPKLKVEVFPFP--;

In column 26, line 46, please delete "(SEQ ID KO:3)" and insert --(SEQ ID NO:3)--;

In column 26, lines 46-47, please delete "LFFFLPVGVLP" and insert --LFFFLPVVNVLP--;

In column 26, lines 49-50, please delete "LKPFPCKVEVFPFP" and insert --LKPFPKLKVEVFPFP--;

UNITED STATES PATENT AND TRADEMARK OFFICE
CERTIFICATE OF CORRECTION

PATENT NO. : 6,852,685 B1
APPLICATION NO. : 09/641802
DATED : February 8, 2005
INVENTOR(S) : Boldogh et al.

It is certified that error appears in the above-identified patent and that said Letters Patent is hereby corrected as shown below:

In column 26, line 62, please delete "(SEQ ID KO:3)" and insert --(SEQ ID NO:3)--;

In column 26, lines 62-63, please delete "LFFFLPVGVLP" and insert --LFFFLPVVNVLP--;

In column 26, line 65, please delete "LKPFPCKVEVFPFP" and insert --LKPFPKLKVEVFPFP--;

In column 27, lines 4-5, please delete "LFFFLPVGVLP" and insert --LFFFLPVVNVLP--;

In column 27, line 20, please delete "(SEQ ID KO:3)" and insert --(SEQ ID NO:3)--;

In column 27, lines 20-21, please delete "LFFFLPVGVLP" and insert --LFFFLPVVNVLP--;

In column 27, line 23, please delete "LKPFPCKVEVFPFP" and insert --LKPFPKLKVEVFPFP--;

In column 27, line 34, please delete "(SEQ ID KO:3)" and insert --(SEQ ID NO:3)--;

In column 27, lines 34-35, please delete "LFFFLPVGVLP" and insert --LFFFLPVVNVLP--;

In column 27, lines 37-38, please delete "LKPFPCKVEVFPFP" and insert --LKPFPKLKVEVFPFP--;

In column 27, line 53, please delete "(SEQ ID KO:3)" and insert --(SEQ ID NO:3)--;

In column 27, lines 53-54, please delete "LFFFLPVGVLP" and insert --LFFFLPVVNVLP--;

In column 27, line 54, please delete "DLEMPVLPVEPFPIFV" and insert --DLEMPVLPVEPFPFV--;

In column 27, lines 56-57, please delete "LKPFPCKVEVFPFP" and insert --LKPFPKLKVEVFPFP--;

In column 28, lines 1-2, please delete "LFFFLPVGVLP" and insert --LFFFLPVVNVLP--;

UNITED STATES PATENT AND TRADEMARK OFFICE
CERTIFICATE OF CORRECTION

PATENT NO. : 6,852,685 B1
APPLICATION NO. : 09/641802
DATED : February 8, 2005
INVENTOR(S) : Boldogh et al.

It is certified that error appears in the above-identified patent and that said Letters Patent is hereby corrected as shown below:

In column 28, line 17, please delete "(SEQ ID KO:3)" and insert --(SEQ ID NO:3)--;

In column 28, line 17-18, please delete "LFFFLPVGVLP" and insert --LFFFLPVVNVLP--;

In column 28, line 20, please delete "LKPFPCKVEVFPFP" and insert --LKPFPKLKVEVFPFP--;

In column 28, line 26, please delete "MIIQPPQPLPPTVMFP" and insert --MHQPPQPLPPTVMFP--;

In column 28, lines 34-35, please delete "LKPFPCKVEVFPFP" and insert --LKPFPKLKVEVFPFP--;

In column 28, line 47, please delete "DQPPDVEKYDLQPFQVQS (SEQ ID KO:3)" and insert --DQPPDVEKPDLQPFQVQS (SEQ ID NO:3)--;

In column 28, lines 47-48, please delete "LFFFLPVGVLP" and insert --LFFFLPVVNVLP--;

In column 28, line 50, please delete "LKPFPCKVEVFPFP" and insert --LKPFPKLKVEVFPFP--;

In column 28, lines 56-57, please delete "LFFFLPVGVLP" and insert --LFFFLPVVNVLP--.

Signed and Sealed this

Thirtieth Day of September, 2008

JON W. DUDAS
*Director of the United States Patent and Trademark Office*

SEQUENCE LISTING

<160> NUMBER OF SEQ ID NOS: 34

<210> SEQ ID NO 1
<211> LENGTH: 7
<212> TYPE: PRT
<213> ORGANISM: Artificial Sequence
<220> FEATURE:

```
<223> OTHER INFORMATION: Description of Artificial Sequence:  synthetic
      peptide

<400> SEQUENCE: 1

Met Gln Pro Pro Pro Leu Pro
 1               5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 2

Leu Gln Thr Pro Gln Pro Leu Leu Gln Val Met Met Glu Pro Gln Gly
 1               5                  10                  15

Asp

<210> SEQ ID NO 3
<211> LENGTH: 18
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 3

Asp Gln Pro Pro Asp Val Glu Lys Pro Asp Leu Gln Pro Phe Gln Val
 1               5                  10                  15

Gln Ser

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 4

Leu Phe Phe Phe Leu Pro Val Val Asn Val Leu Pro
 1               5                  10

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 5

Asp Leu Glu Met Pro Val Leu Pro Val Glu Pro Phe Pro Phe Val
 1               5                  10                  15

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 6
```

```
Met Pro Gln Asn Phe Tyr Lys Leu Pro Gln Met
1               5                   10
```

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: synthetic peptide

<400> SEQUENCE: 7

```
Val Leu Glu Met Lys Phe Pro Pro Pro Gln Glu Thr Val Thr
1               5                   10                  15
```

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: synthetic peptide

<400> SEQUENCE: 8

```
Leu Lys Pro Phe Pro Lys Leu Lys Val Glu Val Phe Pro Phe Pro
1               5                   10                  15
```

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: synthetic peptide

<400> SEQUENCE: 9

```
Val Val Met Glu Val
1               5
```

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: synthetic peptide

<400> SEQUENCE: 10

```
Ser Glu Gln Pro
1
```

<210> SEQ ID NO 11
<211> LENGTH: 3
<212> TYPE: PRT
<213> ORGANISM: Artificial Sequence
<220> FEATURE:
<223> OTHER INFORMATION: Description of Artificial Sequence: synthetic peptide

<400> SEQUENCE: 11

```
Asp Lys Glu
1
```

<210> SEQ ID NO 12
<211> LENGTH: 5
<212> TYPE: PRT
<213> ORGANISM: Artificial Sequence
<220> FEATURE:

<223> OTHER INFORMATION: Description of Artificial Sequence: synthetic
      peptide

<400> SEQUENCE: 12

Phe Pro Pro Pro Lys
 1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 13

Asp Ser Gln Pro Pro Val
 1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 14

Asp Pro Pro Pro Pro Gln Ser
 1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 15

Ser Glu Glu Met Pro
 1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 16

Lys Tyr Lys Leu Gln Pro Glu
 1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 17

Val Leu Pro Pro Asn Val Gly
 1               5

```
<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 18

Val Tyr Pro Phe Thr Gly Pro Ile Pro Asn
 1               5                  10

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 19

Ser Leu Pro Gln Asn Ile Leu Pro Leu
 1               5

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 20

Thr Gln Thr Pro Val Val Val Pro Pro Phe
 1               5                  10

<210> SEQ ID NO 21
<211> LENGTH: 18
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 21

Leu Gln Pro Glu Ile Met Gly Val Pro Lys Val Lys Glu Thr Met Val
 1               5                  10                  15

Pro Lys

<210> SEQ ID NO 22
<211> LENGTH: 18
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 22

His Lys Glu Met Pro Phe Pro Lys Tyr Pro Val Glu Pro Phe Thr Glu
 1               5                  10                  15

Ser Gln

<210> SEQ ID NO 23
<211> LENGTH: 18
<212> TYPE: PRT
<213> ORGANISM: Artificial Sequence
<220> FEATURE:
```

```
<223> OTHER INFORMATION: Description of Artificial Sequence:  synthetic
      peptide

<400> SEQUENCE: 23

Ser Leu Thr Leu Thr Asp Val Glu Lys Leu His Leu Pro Leu Pro Leu
  1               5                  10                  15

Val Gln

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 24

Ser Trp Met His Gln Pro Pro
  1               5

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 25

Gln Pro Leu Pro Pro Thr Val Met Phe Pro
  1               5                  10

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 26

Pro Gln Ser Val Leu Ser
  1               5

<210> SEQ ID NO 27
<211> LENGTH: 22
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 27

Leu Ser Gln Pro Lys Val Leu Pro Val Pro Gln Lys Ala Val Pro Gln
  1               5                  10                  15

Arg Asp Met Pro Ile Gln
                 20

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 28
```

```
Ala Phe Leu Leu Tyr Gln Glu
  1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 29

Arg Gly Pro Phe Pro Ile Leu Val
  1               5

<210> SEQ ID NO 30
<211> LENGTH: 18
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 30

Ala Thr Phe Asn Arg Tyr Gln Asp Asp His Gly Glu Glu Ile Leu Lys
  1               5                  10                  15

Ser Leu

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 31

Val Glu Ser Tyr Val Pro Leu Phe Pro
  1               5

<210> SEQ ID NO 32
<211> LENGTH: 13
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 32

Phe Leu Leu Tyr Gln Glu Pro Val Leu Gly Pro Val Arg
  1               5                  10

<210> SEQ ID NO 33
<211> LENGTH: 3
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 33

Leu Asn Phe
  1

<210> SEQ ID NO 34
<211> LENGTH: 15
```

-continued

```
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 34

Met His Gln Pro Pro Gln Pro Leu Pro Pro Thr Val Met Phe Pro
1               5                   10                  15
```